United States Patent [19]

Keller et al.

[11] 4,019,378
[45] Apr. 26, 1977

[54] HYDRAULIC CHUCKING HEAD

[75] Inventors: Guenter Keller, Ernsthofen; Friedrich Klinger, Garmisch-Partenkirchen; Andreas Pohl, Darmstadt; Gerhard Schimanski, Darmstadt-Eberstadt; Guenter Zuber, Messel, all of Germany

[73] Assignee: Carl Schenck AG, Darmstadt, Germany

[22] Filed: June 7, 1976

[21] Appl. No.: 693,519

[30] Foreign Application Priority Data

July 5, 1975 Germany .......................... 2530132

[52] U.S. Cl. ...................................... 73/103; 279/4
[51] Int. Cl.[2] ......................................... G01N 3/04
[58] Field of Search ................. 73/103; 269/25, 26; 279/4

[56] References Cited

UNITED STATES PATENTS 3,498,121  3/1970  Engelbrecht et al. ............... 73/103
3,908,449  9/1975  Zuber ................................. 73/103

Primary Examiner—Jerry W. Myracle
Attorney, Agent, or Firm—Wolfgang G. Fasse; Willard W. Roberts

[57] ABSTRACT

This hydraulic chucking head, especially for testing machines wherein the test sample must be held without play in the direction of load application, includes at least two test sample holding pistons movable along a common axis toward each other and toward a central axis through the chucking head. These pistons are hollow inside and movable in respective cylinders in the housing with a certain initial play. The piston walls or jackets are elastically yielding when the pressure inside the piston is increased, whereby the test sample is held and simultaneously said play is removed since the piston walls are pressed against the respective cylinder bores. Preferably a non-metallic coating is provided between the piston walls and the cylinder bores which coating acts as a sealing and reduces friction.

7 Claims, 1 Drawing Figure

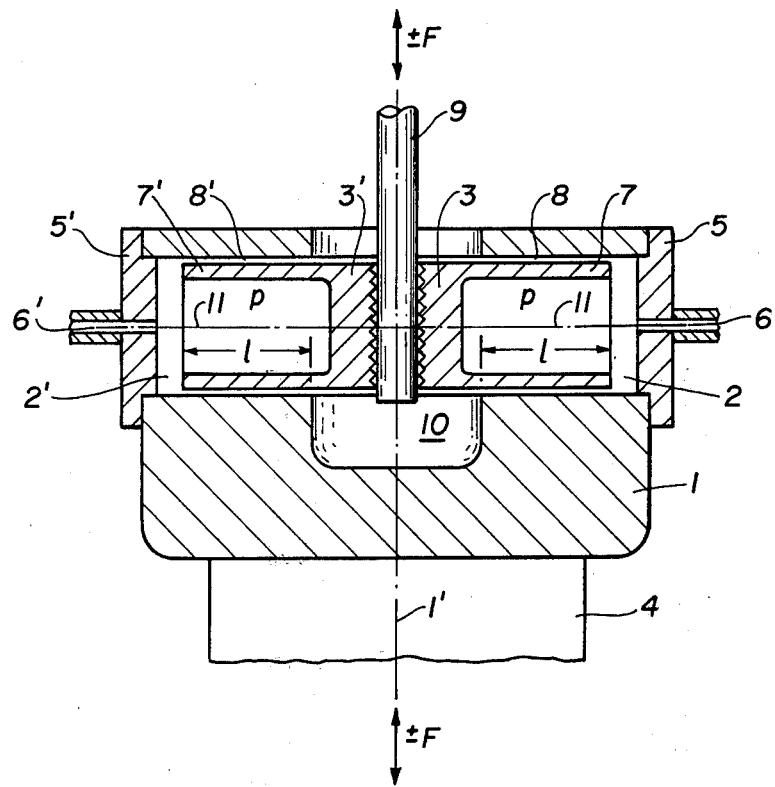

HYDRAULIC CHUCKING HEAD

BACKGROUND OF THE INVENTION

The present invention relates to a chucking head, especially for hydraulic testing machines in which the test sample must be held without play and wherein static or dynamic material testing is performed on the test samples. Such chucking heads have at least two clamping pistons arranged opposite each other for holding a workpiece or test sample in a direction extending substantially at right angles to the direction defined by the longitudinal axis of the clamping pistons.

In material testing machines it is necessary that the clamping devices are suitable for all types of loads to be applied to the test sample, such as a tension force, pressure forces, and dynamic alternating loads or combinations thereof, including slowly varying dynamic loads. Where dynamic loads are used for testing, it is important that the chucking device does not permit any play in the direction in which the dynamic loads are applied. If such play exists, it is difficult to exactly define the load applied to the test sample or workpiece to be tested. Thus, undesirable loads might be applied which must be avoided. In addition, any play may result in a high wear and tear of the chucking device.

U.S. Pat. No. 3,908,449 granted on Sept. 30, 1975 discloses a chucking head operable without play and including two clamping pistons arranged opposite each other. In this known chucking head the play between the clamping pistons in the direction of load application is eliminated by using at least one additional piston which is effective on the clamping pistons in the direction of load application to the probe. The additional piston presses the clamping pistons against the cylinder walls of the clamping cylinders in such a manner that the play between piston and cylinder wall is eliminated in the direction of load application. This known apparatus is very effective, however, it leaves room for improvement, because the use of the additional piston for eliminating the play of the clamping pistons with its supply lines, actuating means and the like makes the clamping device more expensive.

OBJECTS OF THE INVENTION

In view of the above, it is the aim of the present invention to achieve the following objects singly or in combination:

to provide a simple chucking device, especially suitable for testing machines in which play in the load application direction is eliminated without the need for an extra piston for this purpose;

to construct a chucking head with clamping pistons which by their own nature will eliminate the initially present play without the need of additional elements for eliminating the play between the clamping pistons and the respective clamping cylinders;

to provide a chucking head in which the clamping pistons are still movable in an axial direction, that is, in the clamping direction even after the chucking of a workpiece;

to provide a chucking head which is simple in its structure and in its handling; and to improve a chucking head by an intermediate layer between the clamping pistons and the respective clamping cylinders, which will minimize the friction therebetween and thus reducing the wear and tear, as well as any cold welding between the clamping piston wall and the clamping cylinder wall.

SUMMARY OF THE INVENTION:

According to the invention there is provided a chucking head with two clamping pistons movable axially toward each other and away from each other in a housing, whereby the clamping pistons are hollow so that they may be elastically extended by a pressure medium forced into the hollow pistons and into the cylinder holding the respective piston. The application of pressure medium as described fulfills two purposes, namely, to clamp the workpiece in the chucking head and to simultaneously widen the piston jacket thereby eliminating any play between the piston jacket and the cylinder holding the respective piston. This feature of the invention results in an especially simple structure, which is efficient for the intended purpose and does not require any additional elements or devices for the elimination of the piston play. In addition the present device can be actuated in the same manner as conventional devices. Another advantage of the invention is seen in that due to the uniform surface contact between the piston jacket and the respective cylinder walls, corrosion due to friction in the cylinder bore is substantially avoided or at least minimized because of the uniformly distributed surface pressure.

BRIEF FIGURE DESCRIPTION:

In order that the invention may be clearly understood, it will now be described, by way of example, with reference to the single FIGURE which illustrates a central sectional view through a chucking head of the present invention.

DETAILED DESCRIPTION OF EXAMPLE EMBODIMENTS:

The FIGURE illustrates the present chucking head with its essential elements. A housing 1 may be secured to the frame 4 of a testing machine not shown, to hold a test sample 9 as illustrated. The testing force are applied in the direction of the main or first axis 1' of the present head. Normally two such heads will be employed, one at each end of the test sample. One chucking head would be connected to a load applying mechanism, such as a piston cylinder arrangement and the other chucking head would be connected to a load cell or the like which in turn is connected to the frame structure of the testing machine.

The housing 1 is provided with a central recess 10 extending coaxially with the first axis 1'. Two cylinder bores 2 and 2' are also located in the housing and have a longitudinal axis coinciding with a further housing axis 11, which extends at right angles to the first housing axis 1'. The bores 2 and 2' may have a round shape or any other desirable shape. Clamping pistons 3, 3' are located for axial movement in the cylinder bores 2, 2'. According to the invention the clamping pistons 3 and 3' are hollow so that a dead end hole is surrounded by a piston jacket 7, 7' with the open end facing away from the test sample 9 and the closed end facing the test sample 9. The closed end may have a roughened outer surface to securely hold the test sample. As mentioned above, the housing 1 is secured to a rigid member 4 or to the load applying mechanism of a testing machine not shown. Covers 5, 5' close the cylinder bores 2, 2' in the housing 1, whereby cylinder chambers are formed for the clamping pistons 3, 3'. Pressure supply connections 6 and 6' are, for instance, connected to the covers 5, 5' for supplying a pressure medium into the just mentioned chambers for clamping the pistons 3, 3' against the sample 9. Due to the relatively thin pistons walls 7, 7', these walls yield outwardly in an elastic manner to the applied pressure, whereby the pistons are moved toward the test sample 9 and simultaneously the piston walls are expanded outwardly to remove any play between the piston walls and the inner surface of the cylinder chambers.

An intermediate layer 8, 8' is located between the piston walls and the cylinder chamber walls. This intermediate layer is preferably secured to the outer surface of the pistons forming a coating thereon. However, the intermediate layer may, in the alternative form a coating on the inner surface of the cylinder chamber. These layers 8, 8' are of materials which greatly facilitate or improve the frictional characteristics between the piston and respective chamber. These intermediate layers 8, 8' are made of a material having the desired characteristics, for example, synthetic materials such as polytetrafluroethylene (PTFE) or polyimide and similar materials are suitable for the purpose. Rather than providing either the piston or the cylinder walls with the coating, it is possible to provide both surfaces with such a coating. Another advantage of these intermediate layers is seen in that they provide a good sealing for the pressure medium in the above mentioned chambers, so that separate sealing elements between the clamping pistons and the cylinder walls are obviated. In operation, the pressure $p$ in the cylinder chambers 2 and 2' initially moves the clamping pistons 3, 3' in the direction of the axis 11 toward the test sample 9, thereby clamping the test sample into position for applying the test loads. As the pressure $p$ is increased in the chambers 2 and 2', the hollow clamping pistons 3, 3' are elastically widened, whereby the piston jackets 7, 7' are pressed against the inner walls of the cylinder chambers or bores 2, 2', thus eliminating any play between the piston and the respective bore.

By increasing the pressure $p$ still further, it is assured that the clamping pistons rest tightly against the walls of the cylinder bore, even if the maximum testing force is applied. In this manner the sample 9 is held with the necessary clamping force without play in the load direction as indicated by the first axis 1'. Thus, the test sample 9 may now be subjected to the testing forces, such as tension or pressure as indicated by the double arrows and the letter $\pm F$.

When the pressure is released from the chambers 2, 2', the elastic deformation of the piston jackets 7, 7' is removed and the initial play between the cylinder chambers 2, 2' and the pistons 3, 3' is restored, whereby the pistons may be brought back into their starting position, for example, by springs or the like not shown. This return of the pistons into their starting position is assured due to the elastic return into their original shape even if frictional corrosion should have occurred. The initial play between the non-deformed pistons and the inner walls of the cylinder chambers may be selected with due regard to the possible elastic deformation and other design characteristics of the piston cylinder device. By suitably selecting the pressure $p$ in the cylinder chambers 2, 2' as well as the thickness or rather the elasticity of the piston jackets 7, 7' and the play between these jackets and the inner surfaces of the cylinder chambers, and by further selecting the area of the facing surface of each piston as well as its guiding length "$l$" and the friction coefficient between the piston and the cylinder, it is assured that the clamping pistons are still movable in the direction of the axis 11 even after the play between the pistons and the cylinder chambers has been removed. This has the advantage that any deformation of the sample 9 during the clamping and due to the clamping can be compensated. Thus, due to such compensation, the necessary or predetermined clamping force will be maintained in spite of any deformation of the test sample at the clamping point.

Summarizing the foregoing, it must be emphasized that by providing the intermediate layer 8, 8' and by selecting the proper materials for that layer, it is possible to control the sliding characteristics, as well as the frictional characteristics, and the wear and tear characteristics of the piston cylinder units. Especially low frictional and wear and tear characteristics may be achieved by making the intermediate layer 8, 8' from a non-metallic material, such as PTFE. This feature has the further advantage that the synthetic material layer may easily be replaced, if necessary, and that the friction corrosion between clamping piston and cylinder walls is completely eliminated. The intermediate layer also eliminates any cold welding between the piston jackets and the respective cylinder wall. Still another advantage of the intermediate layer is seen in that it acts as a sealing between piston and cylinder, whereby separate sealing elements are obviated.

It has been found that a good guidance for the cylinders is accomplished when the guide length $l$ shown in the figure corresponds approximately to the diameter of the respective piston. This feature assures that the piston is properly guided even at the maximum testing forces extending in the direction of the axis 1' and that the elmination of play is assured even at these maximum testing forces, while simultaneously still permitting the axial displacement of the piston. This feature, as mentioned, compensates for any deformations of the test sample at the clamping point if such deformation should occur, whereby also any variations of the clamping force which might otherwise result from the deformation of the test sample, are also compensated.

Although the invention has been described with reference to specific example embodiments, it is to be understood, that it is intended to cover all modifications and equivalents within the scope of the appended claims.

What is claimed is:

1. A chucking head especially for testing machines to hold a test sample therein, comprising a housing having a first axis, a recess extending coaxially in the direction of said first axis in said housing, at least one second axis in said housing extending at a right angle to said first axis, cylinder bore means in said housing extending along said second axis and having an open end facing into said recess, hollow piston means located in each of said cylinder bore means and facing toward said first axis, and pressure supply means communicating with said cylinder bore means, said hollow piston means being made of elastically yielding material whereby upon application of pressure the piston jackets are pressed against the respective cylinder bore means to eliminate play therebetween.

2. The chucking head according to claim 1, further comprising an intermediate layer between said piston means and the respective cylinder bore means.

3. The chucking head according to claim 2, wherein said intermediate layer is a coating on said piston walls facing the respective cylinder bore means.

4. The chucking head according to claim 2, wherein said intermediate layer is a coating on said cylinder bore means.

5. The chucking head according to claim 2, wherein said intermediate layer is a non-metallic material.

6. The chucking head according to claim 2, wherein said intermediate layer forms a sealing between the piston means and the respective cylinder bore.

7. The chucking head according to claim 1, wherein each piston means has a guide length $l$ corresponding substantially to the diameter of the respective piston means.

* * * * *